(12) United States Patent
Ishida et al.

(10) Patent No.: US 7,732,644 B2
(45) Date of Patent: Jun. 8, 2010

(54) PROCESS FOR PRODUCING α,β-UNSATURATED ALDEHYDE COMPOUNDS

(75) Inventors: Kosaku Ishida, Wakayama (JP); Shigeyoshi Tanaka, Wakayama (JP); Takahiro Asada, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/095,800

(22) PCT Filed: Nov. 8, 2006

(86) PCT No.: PCT/JP2006/322699

§ 371 (c)(1),
(2), (4) Date: Jun. 2, 2008

(87) PCT Pub. No.: WO2007/063703

PCT Pub. Date: Jun. 7, 2007

(65) Prior Publication Data

US 2009/0171124 A1 Jul. 2, 2009

(30) Foreign Application Priority Data

Dec. 1, 2005 (JP) .............................. 2005-348121

(51) Int. Cl.
C07C 45/72 (2006.01)
C07C 29/14 (2006.01)
(52) U.S. Cl. ...................... 568/461; 568/463; 568/862
(58) Field of Classification Search ................. 568/461, 568/463, 862
See application file for complete search history.

(56) References Cited

U.S. PATENT DOCUMENTS

| 4,408,079 | A | * | 10/1983 | Merger et al. | 568/463 |
| 4,496,770 | A | * | 1/1985 | Duembgen et al. | 568/463 |
| 4,929,776 | A | * | 5/1990 | Grosselin et al. | 568/862 |
| 6,552,232 | B2 | * | 4/2003 | Mehnert et al. | 568/463 |

FOREIGN PATENT DOCUMENTS

| EP | 0 058 927 | 9/1982 |
| EP | 0 092 097 | 10/1983 |

OTHER PUBLICATIONS

Ishikavva, et al."Pyrrolidine Catalyzed Homo-Aldol Condensation Reactions of Aldehydes", Synlett, vol. 4, pp. 450-452, XP002421842, (1999).

Lee et al., "Synthesis of Aliphalic Ketones from Allylic Alcohols through Consecutive Isomerization and Chelation-Assisted Hydroacylation by a Rhodium Catalyst", J. Org.Chem., vol. 67, pp. 3945-3948, XP002421843, (2002).

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

The present invention relates to processes for producing α,β-unsaturated aldehyde compounds and unsaturated alcohols with a good yield. There is provided a process for producing and α,β-unsaturated aldehyde compound including the step of subjecting a raw aldehyde compound to an intermolecular condensation reaction in the presence of an amine and a protonic acid having 4 to 20 carbon atoms or a salt thereof; and a process for producing an unsaturated alcohol including the step of subjecting the α,β-unsaturated aldehyde compound to a reduction reaction.

10 Claims, No Drawings

PROCESS FOR PRODUCING α,β-UNSATURATED ALDEHYDE COMPOUNDS

FIELD OF THE INVENTION

The present invention relates to processes for producing α,β-unsaturated aldehyde compounds and unsaturated alcohols.

BACKGROUND OF THE INVENTION

The α,β-unsaturated aldehyde compounds are useful compounds as perfumes, intermediates for perfumes, or raw materials for medicines or agricultural chemicals.

Examples of the α,β-unsaturated aldehyde compounds usable as perfumes include trans-2-hexenal, trans-2-heptenal, trans-2-octenal, trans-2-nonenal, trans-2-decenal, trans-2-undecenal, trans-2-dodecenal, trans-2-tridecenal, 2,4-octadienal, 2,4-nonadienal, 2,6-nonadienal, 2,4-decadienal, 2,4-undecadienal, 2,4-dodecadienal, citral, α-methylenecitronellal ("Bergamal"), cinnamaldehyde (cinnamic aldehyde), α-methyl cinnamaldehyde and α-hexyl cinnamaldehyde.

Also, examples of the α,β-unsaturated aldehyde compounds usable as the intermediates for perfumes include derivatives of campholenic aldehyde which are usable as a raw material for perfumes such as "Sandalmysole core", "Bacdanol" and "Sandalore", derivatives of p-isobutyl benzaldehyde which are usable as a raw material for perfumes such as "Suzaral", and derivatives of p-t-butyl benzaldehyde which are usable as a raw material for perfumes such as "Lilial".

These α,β-unsaturated aldehyde compounds may be produced by various methods. As one of these methods, there is known the method of subjecting a raw aldehyde compound to an intermolecular condensation reaction. In such a method of producing the α,β-unsaturated aldehyde compound by the intermolecular condensation reaction of the raw aldehyde compound, when two different kinds of aldehyde compounds are subjected to cross aldol condensation in the presence of a known aldol condensation catalyst such as sodium hydroxide, the respective aldehyde compounds individually undergo a condensation reaction of same kinds of aldehyde compounds, so that a selectivity of the aimed α,β-unsaturated aldehyde compound by the cross condensation reaction tends to be lowered and, therefore, the purification of the resultant product tends to inevitably become complicated.

There has been described, for example, the method of producing the α,β-unsaturated aldehyde compound by subjecting (A) an aldehyde compound containing a larger number of carbon atoms and (B) an aldehyde compound containing a smaller number of carbon atoms to a cross condensation in an inert solvent in the presence of an organic acid ammonium salt (for example, refer to JP 2004-513871A).

However, the above conventional method has problems such as a relatively large molar ratio of the aldehyde compound (B) to the aldehyde compound (A) (aldehyde compound (B)/aldehyde compound (A)) ranging from 2.5 to 10, necessity of conducting the condensation reaction in a nonpolar solvent capable of forming an azeotropic mixture with water, and unsatisfactory yield of the aimed product. Further, in the above method, as the organic acid ammonium salt catalyst, it is required to use an ammonium salt of a lower organic acid having 1 to 3 carbon atoms such as piperidinyl acetate, pyrrolidinium acetate, ammonium acetate, dimethyl ammonium pyridinyl acetate, morpholine acetate, piperidinyl formate and piperidinyl propionate. In Examples of JP 9-216847A, there is disclosed the method for producing an α-alkyl cinnamaldehyde by using acetic acid as a protonic acid and pyrrolidine as an amine.

SUMMARY OF THE INVENTION

The present invention relates to the following aspects (1) and (2):

(1) A process for producing an α,β-unsaturated aldehyde compound, including the step of subjecting an aldehyde compound to an intermolecular condensation reaction in the presence of an amine and a protonic acid having 4 to 20 carbon atoms or a salt thereof;

(2) A process for producing an unsaturated alcohol including the step of subjecting the α,β-unsaturated aldehyde compound produced by the process as described in the above aspect (1) to a reduction reaction.

DETAILED DESCRIPTION OF THE INVENTION

The above method described in JP 2004-513871A using an inert solvent and further using an ammonium salt of a lower organic acid having 1 to 3 carbon atoms as an organic acid ammonium salt catalyst fails to completely satisfy requirements concerning economy and yield. Also, the method described in JP 9-216847A using acetic acid fails to achieve a satisfactory yield of the aimed product.

The present invention relates to a process for producing an α,β-unsaturated aldehyde compound useful as perfumes or intermediates for perfumes with high yield and productivity, as well as a process for producing an unsaturated alcohol useful as perfumes, etc., by using the unsaturated aldehyde compound.

The inventors have found that upon producing an α,β-unsaturated aldehyde compound by an intermolecular condensation reaction of a raw aldehyde compound, in particular, by a cross condensation reaction thereof, when the condensation reaction is conducted in the presence of an amine and a protonic acid having 4 to 20 carbon atoms or a salt thereof, the α,β-unsaturated aldehyde compound can be produced with a high yield and productivity even without using any solvent, and further that when the α,β-unsaturated aldehyde compound obtained by the above process is subjected to a selective reduction reaction, an unsaturated alcohol useful as perfumes, etc., can be produced.

The process for producing an α,β-unsaturated aldehyde compound according to the present invention is characterized in that the α,β-unsaturated aldehyde compound is produced by subjecting an aldehyde compound to an intermolecular condensation reaction in the presence of an amine and a protonic acid having 4 to 20 carbon atoms or a salt thereof. The respective components and methods used in the above process are explained below.

In the present invention, as the protonic acid having 4 to 20 carbon atoms, there may be used aliphatic and/or aromatic organic acids having 4 to 20 carbon atoms, preferably 6 to 20 carbon atoms, more preferably 8 to 20 carbon atoms and even more preferably 10 to 20 carbon atoms. Examples of the organic acid include butanoic acid, pentanoic acid, hexanoic acid, heptanoic acid, octanoic acid, decanoic acid, dodecanoic acid, stearic acid, isostearic acid, cyclohexanecarboxylic acid, benzoic acid, phthalic acid, maleic acid, monoalkyl-substituted phosphonic acid, dialkyl-substituted phosphinic acid and alkyl-substituted sulfonic acid, dialkyl hydrogen phosphate, alkyl dihydrogen phosphate and alkyl hydrogen sulfate. These organic acids may be used alone or in combination of any two or more thereof. The amount of the organic acid used is preferably from 0.1 to 20 mol % and more preferably from 1 to 5 mol % on the basis of the raw aldehyde compound. Further, an adequate amount of a partially oxidized product of the above raw aldehyde compound may be used in place of separately adding the above organic acid.

On the other hand, examples of the amine usable in combination with the above protonic acid include ammonia, primary amines and secondary amines. Among these amines, preferred are secondary amines. Examples of the secondary amines include dibutyl amine, piperidine, pyrrolidine and proline. Among these amines, especially preferred are dibutylamine and/or piperidine. These amines may be used alone or in combination of any two or more thereof. The amount of the amine used is preferably from 0.1 to 20 mol % and more preferably from 1 to 5 mol % on the basis of the raw aldehyde compound.

In the present invention, the above protonic acid and amine may be added to the reaction system individually or in the form of an amine salt thereof.

In the present invention, as the raw aldehyde compound, there may be used formaldehyde, or compounds having an organic group to which an aldehyde group is bonded. The organic group to which an aldehyde group is bonded is not particularly limited. Examples of the organic group include an alkyl group, an alkenyl group, an alicyclic structure-containing group, an aromatic ring structure-containing group and a heterocyclic structure-containing group. These organic groups may have an adequate substituent group such as a hydroxyl group and an alkoxy group.

The process of the present invention is effectively applied to an intermolecular condensation reaction of the raw aldehyde compound, in particular, a cross condensation reaction of two different kinds of aldehyde compounds.

More specifically, the process of the present invention is applicable to the following process for producing the α,β-unsaturated aldehyde compound by a cross condensation reaction of two different kinds of aldehyde compounds.

In the above process, the two different kinds of aldehyde compounds are aldehyde compounds I and II respectively represented by the general formulae (I) and (II):

R$^1$—CHO (I), and

R$^2$—CHO (II)

wherein R$^1$ and R$^2$ are groups different from each other, and respectively a hydrogen atom, a linear or branched alkyl group having 1 to 20 carbon atoms, a linear or branched alkenyl group having 3 to 20 carbon atoms, an alicyclic structure-containing group having 3 to 20 carbon atoms, an aromatic ring structure-containing group having 6 to 20 carbon atoms or a heterocyclic structure-containing group, and when the aldehyde compound II is HCHO, the resultant α,β-unsaturated aldehyde compound is a compound represented by the general formula (III-a):

(III-a)

wherein R$^{1a}$—C is a residual group of R$^1$ in the general formula (I) which is obtained by removing two hydrogen atoms bonded to a carbon atom being located at the α position of R$^1$ therefrom, and when the aldehyde compound II is a compound other than HCHO, the resultant α,β-unsaturated aldehyde compound is a compound represented by the general formula (III-b):

(III-b)

wherein R$^{2a}$—C is a residual group of R$^2$ in the general formula (II) which is obtained by removing two hydrogen atoms bonded to a carbon atom being located at the α position of R$^2$ therefrom, and R$^1$ is the same as defined above.

The linear or branched alkyl group having 1 to 20 carbon atoms as the above R$^1$ and R$^2$ may have an adequate substituent group such as a hydroxyl group, or may contain a hetero atom such as an ether bond in a molecule thereof. Examples of the linear or branched alkyl group include methyl, ethyl, n-propyl, isopropyl, various butyl groups, various pentyl groups, various hexyl groups, various octyl groups, various decyl groups, various dodecyl groups, various tetradecyl groups, various hexadecyl groups, various octadecyl groups and a hydroxystearyl group.

The linear or branched alkenyl group having 3 to 20 carbon atoms as the above R$^1$ and R$^2$ may have an adequate substituent group such as a hydroxyl group, or may contain a hetero atom such as an ether bond in a molecule thereof. Examples of the linear or branched alkenyl group include allyl, various butenyl groups, various pentenyl groups, various hexenyl groups, various octenyl groups, various decenyl groups, various dodecenyl groups, various tetradecenyl groups, various hexadecenyl groups and various octadecenyl groups.

Examples of the alicyclic structure-containing group having 3 to 20 carbon atoms as the above R$^1$ and R$^2$ include groups containing a monocyclic structure such as a cyclopentane ring, a cyclopentene ring, a cyclopentadiene ring, a cyclohexane ring, a cyclohexene ring and a cyclohexadiene ring, and groups containing a polycyclic structure such as a bicyclopentane ring, a bicyclopentene ring, a bicyclopentadiene ring, a bicycloheptane ring, a bicycloheptene ring, a bicycloheptadiene ring, a bicyclooctane ring, a bicyclooctene ring, a bicyclooctadiene ring, a tricycloundecane ring, a tricycloundecene ring, a tricycloundecadiene ring, a norbornane ring and a norbornene ring. These ring structures may have an adequate substituent group bonded to the ring such as an alkyl group, an alkoxy group and a hydroxyl group.

Examples of the aromatic ring structure-containing group having 6 to 20 carbon atoms as the above R$^1$ and R$^2$ include aryl groups having 6 to 20 carbon atoms and arylalkyl groups having 7 to 20 carbon atoms. These aromatic ring structure-containing groups may have an adequate substituent group bonded to the aromatic ring such as an alkyl group, an alkoxy group or a hydroxyl group. Specific examples of the aryl groups having 6 to 20 carbon atoms include phenyl, naphthyl, tolyl, xylyl, ethylphenyl, isobutylphenyl, tert-butylphenyl, methoxyphenyl and ethoxyphenyl. Specific examples of the arylalkyl groups having 7 to 20 carbon atoms include benzyl, various alkylbenzyl groups, phenethyl, various alkylphenethyl groups, phenylpropyl, various alkylphenylpropyl groups, naphthylmethyl, various alkylnaphthylmethyl groups, naphthylethyl, various alkylnaphthylethyl groups, naphthylpropyl and various alkylnaphthylpropyl groups.

Examples of the heterocyclic structure-containing group as the above R$^1$ and R$^2$ include those groups having a hetero ring containing an oxygen atom as a hetero atom such as a furan ring, a dihydrofuran ring, a tetrahydrofuran ring, a pyran ring, a dihydropyran ring and a tetrahydropyran ring. These heterocyclic structures may have an adequate substituent group bonded to the hetero ring such as an alkyl group, an alkoxy group or a hydroxyl group.

Examples of the aldehyde compounds I and II used as the raw aldehyde compound in the present invention include formaldehyde, acetaldehyde, propanal, butanal, pentanal, 2-methyl butanal, hexanal, octanal, undecanal, 2-methyl octanal, 3,5,5-trimethyl hexanal, cis-3-hexenal ("Leaf aldehyde"), 4-heptenal, 2,6-dimethyl-5-heptenal ("Melonal"), 4-decenal, 2,5,6-trimethyl-4-heptenal, 10-undecenal, citronellal, hydroxyl citronellal, campholenic aldehyde, perillaaldehyde, cyclocitral, "Safranal", "Lyral", trimethylcyclohexenemethyl butanal ("Cetonal"), 3-propylbicyclo[2.2.1]-5-heptene-2-carboxyaldehyde, centenal, benzaldehyde, cuminaldehyde, phenyl acetaldehyde, 2-phenyl propanal, phenyl propionaldehyde, p-isobutyl benzaldehyde, p-t-butyl benzaldehyde, salicylaldehyde, anisaldehyde, vanillin, furfural and 5-hydroxymethyl-2-furfural. The aldehyde compounds I and II to be used may be appropriately selected from these compounds.

The ratio between the aldehyde compounds I and II used in the cross condensation reaction may be controlled such that the aldehyde compound II is used in an amount of from 0.1 to 10 mol, preferably from 0.3 to 3 mol and more preferably from 0.6 to 1.6 mol per 1 mol of the aldehyde compound I.

When HCHO (formaldehyde) is used as the aldehyde compound II, the compound represented by the above general formula (III-a) is produced as the α,β-unsaturated aldehyde compound. In the general formula (III-a), $R^{1a}$—C represents a residual group of $R^1$ in the general formula (I) which is obtained by removing two hydrogen atoms bonded to a carbon atom being located at the a position of $R^1$ therefrom.

On the other hand, when a compound other than HCHO is used as the aldehyde compound II, the compound represented by the above general formula (III-b) is produced as the α,β-unsaturated aldehyde compound. In the general formula (III-b), $R^{2a}$—C represents a residual group of $R^2$ in the general formula (II) which is obtained by removing two hydrogen atoms bonded to a carbon atom being located at the α position of $R^2$ therefrom, and $R^1$ is the same as defined above.

In the present invention, the following condensation reactions I and II are preferably used in the cross condensation between the above aldehyde compounds I and II.

[Condensation Reaction I]

In the condensation reaction I, the α,β-unsaturated aldehyde compound is produced by subjecting a compound represented by the general formula (I) in which $R^1$ is a linear or branched alkyl group having 6 to 20 carbon atoms, a linear or branched alkenyl group having 6 to 20 carbon atoms or an alicyclic structure-containing group having 6 to 20 carbon atoms as the aldehyde compound I and a compound represented by the general formula (II) in which $R^2$ is a hydrogen atom, a linear or branched alkyl group having 1 to 6 carbon atoms, a linear or branched alkenyl group having 3 to 6 carbon atoms or an alicyclic structure-containing group having 3 to 6 carbon atoms as the aldehyde compound II to a condensation reaction.

In the condensation reaction I, as the aldehyde compound I, there may be used a compound represented by the general formula (I) in which $R^1$ is a (2,2,3-trimethylcyclopent-3-en-1-yl)methyl group, such as campholenic aldehyde, as well as n-undecanal, n-octanal, hydroxycitronellal, etc. Further, as the aldehyde compound II, there may be used a compound represented by the general formula (II) in which $R^2$ is a hydrogen atom, methyl, ethyl or the like, such as formaldehyde, acetaldehyde and propionaldehyde.

In the condensation reaction I, the aldehyde compound II is used in an amount of preferably from 1.0 to 10 mol, more preferably from 1.0 to 5 mol and even more preferably from 1.0 to 3 mol per 1 mol of the aldehyde compound I. The reaction temperature is usually from about 20 to about 150° C., preferably from 50 to 130° C. and more preferably from 70 to 120° C. Upon the condensation reaction I, whole amounts of the aldehyde compounds I and II may be added at one time to react with each other. Alternatively, the aldehyde compound II may be dropped to the aldehyde compound I to gradually react with each other.

The use of a solvent in the above condensation reaction is not particularly required. However, if required for any reason such as easiness of handling in the process, a suitable solvent may be used therein. Also, the removal of water produced during the reaction is not particularly required. However, if water should be removed for any reasons upon carrying out the process, a dehydration procedure may be conducted.

When campholenic aldehyde represented by the formula (I) and propionaldehyde represented by the formula (2) are used as the aldehyde compounds I and II, respectively, 2-methyl-4-(2,2,3-trimethylcyclopent-3-en-1-yl)-but-2-en-1-al represented by the formula (3) is produced according to the following reaction formula.

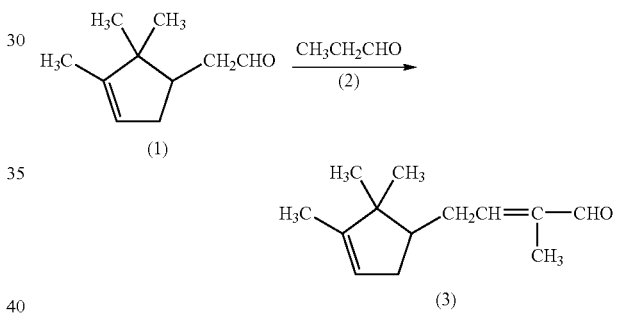

Also, when n-undecanal represented by the formula (4) and formaldehyde are used as the aldehyde compounds I and II, respectively, α-methyleneundecanal represented by the formula (5) is produced according to the following reaction formula.

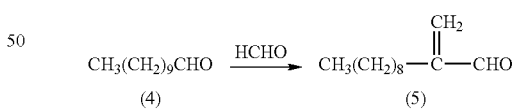

Examples of the α,β-unsaturated aldehyde compounds produced by the condensation reaction I which are usable as perfumes, include trans-2-octenal, trans-2-nonenal, trans-2-decenal, trans-2-undecenal, trans-2-dodecenal, trans-2-tridecenal, trimethyl decadienal, α-methylene citronellal ("Bergamal").

Also, examples of the α,β-unsaturated aldehyde compounds produced by the condensation reaction I which are usable as intermediates for perfumes, include α-methylene undecanal, α-methylene octanal, α-methylene hydroxycitronellal, 2-methyl-2-decenal, 2-methyl-2-undecenal and 2-methyl-4-(2,2,3-trimethylcyclopent-3-en-1-yl)-but-2-en-1-al.

[Condensation Reaction II]

In the condensation reaction II, the α,β-unsaturated aldehyde compound is produced by subjecting a compound represented by the general formula (I) in which $R^1$ is an aromatic ring structure-containing group having 6 to 20 carbon atoms or a heterocyclic structure-containing group as the aldehyde compound I and a compound represented by the general formula (II) in which $R^2$ is a hydrogen atom, a linear or branched alkyl group having 1 to 10 carbon atoms or a linear or branched alkenyl group having 3 to 10 carbon atoms as the aldehyde compound II to a condensation reaction.

Examples of the aldehyde compound I usable in the condensation reaction I include benzaldehyde, cuminaldehyde, p-isobutyl benzaldehyde, p-t-butyl benzaldehyde and phenyl acetaldehyde. Examples of the aldehyde compound II usable in the condensation reaction II include acetaldehyde, propionaldehyde, isobutanal, isopentanal, pentanal and octanal.

In the condensation reaction II, the aldehyde compound I is used in an amount of preferably from 0.4 to 2.5 mol and more preferably from 0.6 to 2.0 mol per 1 mol of the aldehyde compound II.

The reaction temperature is usually from about 70 to about 140° C. and preferably from 100 to 120° C.

Upon the condensation reaction II, whole amounts of the aldehyde compounds I and II may be added at one time to react with each other. Alternatively, the aldehyde compound II may be dropped to the aldehyde compound I to gradually react with each other.

When p-isobutyl (or t-butyl)benzaldehyde represented by the formula (6) and propionaldehyde represented by the formula (2) are used as the aldehyde compounds I and II, respectively, p-isobutyl (or t-butyl)-α-methyl cinnamaldehyde represented by the formula (7) is produced according to the following reaction formula.

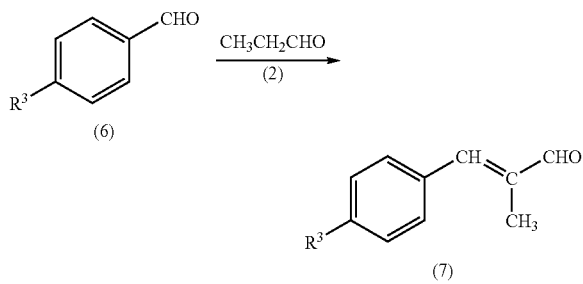

In the formulae (6) and (7), $R^3$ represents isobutyl or t-butyl.

The thus obtained α,β-unsaturated aldehyde compound is hydrogenated to produce p-isobutyl (or t-butyl)-α-methyl hydrocinnamaldehyde as a perfume (i.e., "Suzaral" as the compound containing the isobutyl group; and "Lilial" as the compound containing the t-butyl group).

Also, when phenyl acetaldehyde represented by the formula (8) and isobutanal (n=0) or isopentanal (n=1) represented by the formula (9) are used as the aldehyde compounds I and II, respectively, 4-methyl-2-phenyl-2-pentenal (n=0) and 5-methyl-2-phenyl-2-hexenal (n=1), which are perfumes represented by the formula (10), are respectively produced according to the following reaction formula.

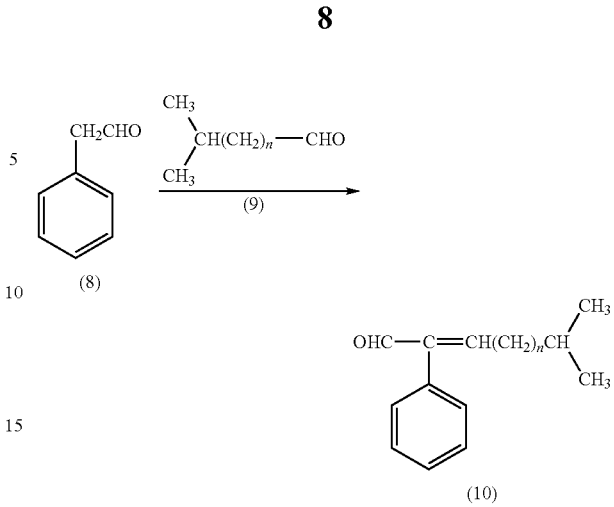

In the formulae (9) and (10), n represents a number of 0 or 1.

Examples of the α,β-unsaturated aldehyde compounds produced by the condensation reaction II which are usable as perfumes, include cinnamaldehyde, α-methyl cinnamaldehyde, 4-methyl-2-phenyl-2-pentenal, 5-methyl-2-phenyl-2-hexenal, α-amyl cinnamaldehyde, α-hexyl cinnamaldehyde and o-methoxy cinnamaldehyde.

Also, examples of the α,β-unsaturated aldehyde compounds produced by the condensation reaction II which are usable as intermediates for perfumes, include p-isopropyl-α-methyl cinnamaldehyde (which can be converted into cyclamen aldehyde as a perfume by hydrogenation thereof), p-isobutyl-α-methyl cinnamaldehyde and p-t-butyl-α-methyl cinnamaldehyde.

In accordance with the present invention, there is also provided a process for producing an unsaturated alcohol by subjecting the α,β-unsaturated aldehyde compound produced by the above process of the present invention to selective reduction reaction.

The reducing agent used for the selective reduction reaction is preferably an aluminum alcoholate or a metal hydride compound. Examples of the aluminum alcoholate include aluminum methylate, aluminum ethylate, aluminum propylate, aluminum isopropylate, aluminum butylate and aluminum isobutylate. These reducing agents may be used alone or in combination of any two or more thereof. Among these reducing agents, aluminum isopropylate is preferred in view of a good yield.

Examples of the metal hydride compound include aluminum hydride compounds and boron hydride compounds. Specific examples of the aluminum hydride compounds include lithium aluminum hydride, lithium alkoxyaluminum hydride, sodium aluminum hydride, sodium ethoxyaluminum hydride, magnesium aluminum hydride and dialkyl aluminum hydride. These aluminum hydride compounds may be used alone or in combination of any two or more thereof. When the aluminum hydride compound is used as the reducing agent, the selective reduction reaction is preferably conducted, for example, using an inert solvent such as diethyl ether, dibutyl ether, tetrahydrofuran and dioxane.

Specific examples of the boron hydride compounds include sodium borohydride, lithium borohydride, potassium borohydride and aluminum borohydride. These boron hydride compounds may be used alone or in combination of any two or more thereof. When the boron hydride compound is used as the reducing agent, the selective reduction reaction is preferably conducted using a lower aliphatic alcohol as a reaction solvent. Specific examples of the reaction solvent usable in the selective reduction reaction include methyl alcohol, ethyl alcohol, isopropyl alcohol, and aqueous alcohols, e.g., mixed solvents such as water/methyl alcohol, water/ethyl alcohol and water/isopropyl alcohol.

When the aluminum alcoholate is used as the reducing agent, the reducing temperature is usually from about 50 to about 120° C. and preferably from 80 to 110° C. When the metal hydride compound is used as the reducing agent, the reducing temperature is usually from about 20 to about 30° C. and preferably from 10 to 20° C.

In the above selective reduction, for example, 2-methyl-4-(2,2,3-trimethylcyclopent-3-en-1-yl)-but-2-en-1-al is converted to 2-methyl-4-(2,2,3-trimethylcyclopent-3-en-1-yl)-but-2-en-1-ol ("Sandalmysole core"). This compound has a sandalwood-like scent and, therefore, is suitable as a perfume material.

Also, 2-ethyl-4-(2,2,3-trimethylcyclopent-3-en-1-yl)-but-2-en-1-al as the $\alpha,\beta$-unsaturated aldehyde compound obtained by subjecting campholenic aldehyde represented by the formula (I) and butanal to a condensation reaction, is converted to 2-ethyl-4-(2,2,3-trimethylcyclopent-3-en-1-yl)-but-2-en-1-ol (bacdanol) by the same selective reduction method. This compound is suitable as a synthetic perfume having a sandalwood-like scent.

The perfume composition in which the unsaturated alcohol such as sandal mysole core or bacdanol obtained in the present invention is blended can effectively generate a sandalwood-like scent. The effective blending ratio of the unsaturated alcohol in the perfume composition extensively varies depending upon configuration, kind and application or purpose of products to which the perfume composition is applied. For example, when the unsaturated alcohol is blended in an amount of 0.5 to 30%, an interesting effect can be attained. However, the concentration of the unsaturated alcohol in the perfume composition may be out of the above-specified range. The formulation of the perfume composition containing sandal mysole core is exemplified below.

The following examples further describe and demonstrate embodiments of the present invention. The examples are given solely for the purpose of illustration and are not to be construed as limitations of the present invention.

FORMULATION EXAMPLE

Perfume Composition for Shampoo 5 parts by mass of sandal mysole core was added to 95 parts by mass of a perfume composition containing respective components shown below, thereby obtaining a perfume composition for shampoo having a sandalwood-like soft scent.

| Blending Components | part by mass |
| --- | --- |
| Linalool | 15 |
| Cyclopentadecanolide | 12 |
| Methyldihydrojasmonate | 12 |
| p-t-Butyl-α-methylhydrocinnamic aldehyde | 10 |
| Cis-3-hexenyl salicylate | 10 |
| Dimethylbenzylcarbinyl acetate | 5 |
| Citronellol | 5 |
| Phenylethyl alcohol | 5 |
| AMBER CORE* | 5 |
| α-n-hexyl cinnamic aldehyde | 4 |
| Benzyl acetate | 4 |
| Orange oil | 3 |

| Blending Components | part by mass |
| --- | --- |
| Linalyl acetate | 3 |
| γ-Methyl ionone | 2 |
| Total | 95 |

Note:
*Tradename of product available from Kao Corporation; compound name: 1-(2-t-butylcyclohexyloxy)-2-butanol According to the present invention, $\alpha,\beta$-unsaturated aldehyde compounds useful as perfumes or intermediates for perfumes can be produced with high yield and productivity. Further, unsaturated alcohols useful as perfumes, etc., can be produced from the unsaturated aldehyde compounds.

Example 1

A 500 mL four-necked flask equipped with a stirrer, a thermometer, a reflux condenser and a dropping funnel was charged with 171 g (0.98 mol) of campholenic aldehyde (purity: 88%), 3.8 g (0.045 mol) of piperidine and 13.1 g (0.046 mol) of stearic acid, and the contents in the flask were stirred while heating at 100° C. Then, 91 g (1.6 mol) of propionaldehyde was gradually dropped into the flask for 6 h, and the resultant mixture was aged for 1 h and then cooled. Thereafter, 3.2 g (0.053 mol) of acetic acid was added to the mixture to remove amines therefrom, thereby separating the mixture into two layers. The thus separated organic layer was washed with water and separated into two layers, thereby obtaining 295 g (0.93 mol) of 2-methyl-4-(2,2,3-trimethylcyclopent-3-en-1-yl)-but-2-en-1-al (purity as measured by gas chromatography: 60.6%) (yield based on theoretical amount: 95%).

Example 2

A 500 mL four-necked flask equipped with a stirrer, a thermometer, a reflux condenser and a dropping funnel was charged with 171 g (0.98 mol) of campholenic aldehyde (purity: 88%), 5.8 g (0.045 mol) of dibutyl amine and 5.3 g (0.046 mol) of hexanoic acid, and the contents in the flask were stirred while heating at 100° C. Then, 91 g (1.6 mol) of propionaldehyde was gradually dropped into the flask for 6 h, and the resultant mixture was aged for 1 h and then cooled. Thereafter, 3.2 g (0.053 mol) of acetic acid was added to the mixture to remove amines therefrom, thereby separating the mixture into two layers. The thus separated organic layer was washed with water and further separated into two layers, thereby obtaining 280 g (0.92 mol) of 2-methyl-4-(2,2,3-trimethylcyclopent-3-en-1-yl)-but-2-en-1-al (purity as measured by gas chromatography: 63.4%) (yield based on theoretical amount: 94%).

Example 3

A 3 L four-necked flask equipped with a stirrer, a thermometer and a reflux condenser was charged with 1043 g (6.0 mol) of n-undecanal, 520 g (6.4 mol) of a 37% by mass formaldehyde aqueous solution, 47 g (0.36 mol) of dibutyl amine and 33 g (0.11 mol) of stearic acid, and the contents in the flask were stirred while heating at 95° C. After the elapse of 30 min. it was confirmed that no n-undecanal was present in the raw mixture, and then the mixture was cooled and separated into two layers. The thus separated organic layer was subjected to distillation treatment, thereby obtaining 1062 g (5.7 mol) of α-methylene undecanal (purity as measured by gas chromatography: 97%) (yield based on theoretical amount: 95%).

Example 4

A 2 L four-necked flask equipped with a stirrer, a thermometer and a reflux condenser was charged with 762 g (6.0 mol) of n-octanal, 520 g (6.4 mol) of a 37% by mass formaldehyde aqueous solution, 15 g (0.33 mol) of dibutyl amine and 10 g (0.06 mol) of decanoic acid, and the contents in the flask were stirred while heating at 95° C. After the elapse of 45 min, it was confirmed that no n-octanal was present in the raw mixture, and then the mixture was cooled and separated into two layers. The thus separated organic layer was subjected to distillation treatment, thereby obtaining 790 g (5.4 mol) of a-methylene octanal (purity as measured by gas chromatography: 95%) (yield based on theoretical amount: 90%).

Example 5

A 3 L four-necked flask equipped with a stirrer, a thermometer and a reflux condenser was charged with 1032 g (6.0 mol) of hydroxycitronellal, 520 g (6.4 mol) of a 37% by mass formaldehyde aqueous solution, 53 g (0.41 mol) of dibutyl amine and 10 g (0.09 mol) of hexanoic acid, and the contents in the flask were stirred while heating at 95° C. After the elapse of 40 min, it was confirmed that no hydroxycitronellal was present in the raw mixture, and then the mixture was cooled and separated into two layers. The thus separated organic layer was subjected to distillation treatment, thereby obtaining 1058 g (5.5 mol) of 3,7-dimethyl-2-methylene-7-hydroxyoctanal (purity as measured by gas chromatography: 95%) (yield based on theoretical amount: 92%).

Comparative Example 1

A 500 mL four-necked flask equipped with a stirrer, a thermometer, a reflux condenser and a dropping funnel was charged with 171 g (0.98 mol) of campholenic aldehyde (purity: 88%), 3.8 g (0.045 mol) of piperidine and 2.8 g (0.046 mol) of acetic acid, and the contents in the flask were stirred while heating at 100° C. Then, 92 g (1.6 mol) of propionaldehyde was gradually dropped into the flask for 6 h, and the resultant mixture was aged for 1 h and then cooled. Thereafter, 3.2 g (0.053 mol) of acetic acid was added to the mixture to remove amines therefrom, thereby separating the mixture into two layers. The thus separated organic layer was washed with water and separated into two layers, thereby obtaining 279 g (0.79 mol) of 2-methyl-4-(2,2,3-trimethylcyclopent-3-en-1-yl)-but-2-en-1-al (purity as measured by gas chromatography: 54.7%) (yield based on theoretical amount: 81%).

Comparative Example 2

A 10 L glass reactor was charged with 3.04 kg (17 mol) of campholenic aldehyde (purity:85%) and 2 kg of toluene, and further 2.9 kg (50 mol) of propionaldehyde (purity:100%), 170 g (2 mol) of piperidine and 120 g (2 mol) of glacial acetic acid were added to the flask at room temperature while stirring. Next, the resultant mixture was refluxed for 4 h using a water separator to remove 680 mL of a reaction water through a circulating path of the reaction system. As a result of analyzing a sample of the obtained reaction mixture by a gas chromatography, it was confirmed that the content of unreacted extracts in the reaction mixture was 15% by mass.

According to the amount of the unreacted extracts, 85 g (1 mol) of piperidine and 60 g (1 mol) of glacial acetic acid were further added to the reaction mixture. The obtained mixture was further refluxed for 1 h, and then 120 g of a reaction water was removed through a circulating path of the reaction system, thereby allowing the extracts to be completely reacted. After distilling off 1.9 kg of toluene, the resultant reaction mixture was washed with 2 L of water twice. Thereafter, 6.24 kg of an organic layer separated from the reaction mixture was subjected to distillation treatment in a 30 cm packed column, thereby obtaining 3.27 kg (14.5 mol) of the reaction product (purity as measured by gas chromatography: 85%) (yield based on theoretical amount: 85%).

As a result, it was confirmed that when using acetic acid having 2 carbon atoms as an aliphatic acid having less than 4 carbon atoms, even though the reaction water was removed, the resultant compound failed to be produced with a yield as high as that in the present invention.

Example 6

2-Methyl-4-(2,2,3-trimethylcyclopent-3-en-1-yl)-but-2-en-1-al as the α,β-unsaturated aldehyde obtained in Example 1 was purified by distillation, and then subjected to the following selective reduction reaction to obtain an unsaturated alcohol.

A 1000 mL flask equipped with a thermometer, a stirrer and a dropping funnel was charged with 500 mL of anhydrous ethyl ether and 7.5 g (0.2 mol) of lithium aluminum hydride, and then while violently stirring the resultant mixture, 96 g (0.5 mol) of the purified α,β-unsaturated aldehyde was added thereto for 1 h. During the addition, the flask used for the reaction was cooled with a mixture of ice and a common salt to maintain the reaction temperature at 15 to 20° C. Further, the resultant reaction mixture was stirred at room temperature for 2 h, and then ice was added thereto to hydrolyze lithium aluminum hydride.

Next, a 5% by mass sulfuric acid aqueous solution was added to the reaction mixture to decompose aluminum hydroxide, and then extracted with 50 mL of ether 3 times using a separating funnel. The thus obtained ether layer was washed with water, dried and then subjected to distillation treatment to remove ether therefrom, thereby obtaining a crude product of 2-methyl-4-(2,2,3-trimethylcyclopent-3-en-1-yl)-but-2-en-1-ol (yield based on theoretical amount: 85%).

INDUSTRIAL APPLICABILITY

The thus obtained crude product was fractionated to obtain purified 2-methyl-4-(2,2,3-trimethylcyclopent-3-en-1-yl)-but-2-en-1-ol. As a result, it was confirmed that the thus obtained 2-methyl-4-(2,2,3-trimethylcyclopent-3-en-1-yl)-but-2-en-1-ol had a sandalwood-like scent and, therefore, was excellent as a perfume material.

The present invention relates to a process for producing an α,β-unsaturated aldehyde compound useful as perfumes or intermediates for perfumes; and a process for producing an unsaturated alcohol useful as perfumes, etc., by using the α,β-unsaturated aldehyde compound.

The invention claimed is:
1. A process for producing an α,β-unsaturated aldehyde compound, comprising:
subjecting two different aldehyde compounds to a cross condensation reaction in the presence of an amine and a protonic acid having 6 to 20 carbon atoms or a salt thereof;

wherein the two different aldehyde compounds are aldehyde compound I and aldehyde compound II represented by formula (I) and formula (II) respectively $$R^1\text{—CHO} \tag{I}$$

$$R^2\text{—CHO} \tag{II}$$

wherein $R^1$ and $R^2$ are different;

$R^1$ is a linear or branched alkyl group having 6 to 20 carbon atoms, a linear or branched alkenyl group having 6 to 20 carbon atoms, or an alicyclic structure-containing group having 6 to 20 carbon atoms; and $R^2$ is a hydrogen atom, a linear or branched alkyl group having 1 to 6 carbon atoms, a linear or branched alkenyl group having 3 to 6 carbon atoms, or an alicyclic structure-containing group having 3 to 6 carbon atoms; or $R^1$ is an aromatic ring structure-containing group having 6 to 20 carbon atoms, or a heterocyclic structure-containing group; and $R^2$ is a hydrogen atom, a linear or branched alkyl group having 1 to 10 carbon atoms, or a linear or branched alkenyl group having 3 to 10 carbon atoms; and when the aldehyde compound II is HCHO, the resultant α,β-unsaturated aldehyde compound is a compound represented by formula (III-a)

wherein $R^{1a}$—C is a residual group of $R^1$ in the formula (I) which is obtained by removing two hydrogen atoms bonded to a carbon atom being located at the α position of $R^1$ therefrom; and when the aldehyde compound II is an aldehyde compound other than HCHO, the resultant α,β-unsaturated aldehyde compound is a compound represented by formula (III-b)

wherein $R^{2a}$—C is a residual group of $R^2$ in the formula (II) which is obtained by removing two hydrogen atoms bonded to a carbon atom being located at the α position of $R^2$ therefrom, and $R^1$ is as defined in formula (I).

2. The process according to claim 1, wherein the aldehyde compound I is a compound represented by the formula (I) in which $R^1$ is a linear or branched alkyl group having 6 to 20 carbon atoms, a linear or branched alkenyl group having 6 to 20 carbon atoms or an alicyclic structure-containing group having 6 to 20 carbon atoms, and the aldehyde compound II is a compound represented by the formula (II) in which $R^2$ is a hydrogen atom, a linear or branched alkyl group having 1 to 6 carbon atoms, a linear or branched alkenyl group having 3 to 6 carbon atoms or an alicyclic structure-containing group having 3 to 6 carbon atoms.

3. The process according to claim 2, wherein the aldehyde compound II is used in an amount of 1.0 to 10 mol per 1 mol of the aldehyde compound I.

4. The process according to claim 2, wherein the aldehyde compound I is a compound represented by the formula (I) in which $R^1$ is a (2,2,3-trimethylcyclopent-3-en-1-yl)methyl group.

5. The process according to claim 2, wherein the aldehyde compound II is a compound represented by the formula (II) in which $R^2$ is a hydrogen atom, methyl or ethyl.

6. The process according to claim 1, wherein the aldehyde compound I is a compound represented by the formula (I) in which $R^1$ is an aromatic ring structure-containing group having 6 to 20 carbon atoms or a heterocyclic structure-containing group, and the aldehyde compound II is a compound represented by the formula (II) in which $R^2$ is a hydrogen atom, a linear or branched alkyl group having 1 to 10 carbon atoms or a linear or branched alkenyl group having 3 to 10 carbon atoms.

7. The process according to claim 6, wherein the aldehyde compound I is used in an amount of 0.4 to 2.5 mol per 1 mol of the aldehyde compound II.

8. The process according to claim 1, wherein the amine or the salt thereof is a secondary amine or a salt thereof.

9. A process for producing an unsaturated alcohol comprising subjecting the α,β-unsaturated aldehyde compound produced by the process as defined in claim 1 to a reduction reaction.

10. The process according to claim 1, wherein the protonic acid having 6 to 20 carbon atoms is at least one selected from the group consisting of an aliphatic organic acid having 6 to 20 carbon atoms and an aromatic organic acid having 6 to 20 carbon atoms.

* * * * *